United States Patent
Winshtein et al.

(10) Patent No.: US 10,052,218 B2
(45) Date of Patent: Aug. 21, 2018

(54) DEVICES AND METHODS FOR DEPLOYING IMPLANTABLE SLEEVES OVER BLOOD VESSELS

(75) Inventors: Ronny Winshtein, Ramat-HaSharon (IL); Eyal Orion, Ramat-Efal (IL)

(73) Assignee: Vascular Graft Solutions Ltd., Tel-Aviv (IL)

(*) Notice: Subject to any disclaimer, the term of this patent is extended or adjusted under 35 U.S.C. 154(b) by 215 days.

(21) Appl. No.: 14/112,248

(22) PCT Filed: Apr. 17, 2012

(86) PCT No.: PCT/IL2012/050139
§ 371 (c)(1),
(2), (4) Date: Oct. 17, 2013

(87) PCT Pub. No.: WO2012/143925
PCT Pub. Date: Oct. 26, 2012

(65) Prior Publication Data
US 2014/0052234 A1    Feb. 20, 2014

Related U.S. Application Data

(60) Provisional application No. 61/476,347, filed on Apr. 18, 2011.

(51) Int. Cl.
*A61F 2/06* (2013.01)
*A61F 2/95* (2013.01)
(Continued)

(52) U.S. Cl.
CPC ............. *A61F 2/95* (2013.01); *A61F 2/06* (2013.01); *A61F 2/90* (2013.01); *A61B 17/11* (2013.01);
(Continued)

(58) Field of Classification Search
CPC ............ A61B 17/11; A61B 2017/1107; A61B 2017/1132; A61B 2017/1135;
(Continued)

(56) References Cited

U.S. PATENT DOCUMENTS 4,158,984 A    6/1979  Griffiths
4,173,689 A    11/1979 Lyman et al.
(Continued)

FOREIGN PATENT DOCUMENTS

CA    2502504 A1    11/1995
CA    2523812 A1    11/2004
(Continued)

OTHER PUBLICATIONS

International Search Report and the Written Opinion dated Oct. 1, 2012 From the International Searching Authority Re. Application No. PCT/IL2012/050139.
(Continued)

*Primary Examiner* — Ryan J Severson
*Assistant Examiner* — Christian Knauss
(74) *Attorney, Agent, or Firm* — Clements Bernard Walker PLLC; Christopher L. Bernard (57) ABSTRACT

In an aspect of some embodiments there is provided apparatuses and methods including a sleeve expander capable of covering with an implantable sleeve an exterior of a bodily vessel, along a chosen length thereof, the sleeve expander configured to maintain at least a portion of the implantable sleeve in an expanded size greater than a cross sectional dimension thereof when in apposition to the exterior. In some embodiments of the present invention, the apparatus further includes a cutting mechanism configured to cut down the implantable sleeve and/or external fixating means configured to fixate a covering section of the implantable sleeve to a corresponding covered section of the bodily vessel.

22 Claims, 7 Drawing Sheets

(51) Int. Cl.
*A61F 2/90* (2013.01)
*A61B 17/32* (2006.01)
*A61B 17/11* (2006.01)
*A61B 17/22* (2006.01)

(52) U.S. Cl.
CPC ....... *A61B 17/32* (2013.01); *A61B 2017/1107* (2013.01); *A61B 2017/1139* (2013.01); *A61B 2017/22038* (2013.01); *A61F 2/064* (2013.01); *A61F 2220/0075* (2013.01)

(58) Field of Classification Search
CPC ......... A61B 2017/1139; A61B 17/1114; A61B 17/1128; A61B 17/1146; A61B 17/32; A61B 17/320016; A61B 17/32053; A61B 17/320783; A61B 2017/1125; A61F 2/062; A61F 2/07; A61F 2/04; A61F 2/06; A61F 2/064; A61F 2/82; A61F 2/90; A61F 2/95; A61F 2220/0008
See application file for complete search history.

(56) References Cited

U.S. PATENT DOCUMENTS

| | | | |
|---|---|---|---|
| 4,466,139 A | 8/1984 | Ketharanathan | |
| 4,655,771 A | 4/1987 | Wallsten | |
| 4,743,251 A * | 5/1988 | Barra | A61F 2/06 600/36 |
| 5,084,065 A | 1/1992 | Weldon et al. | |
| 5,468,242 A | 11/1995 | Reisberg | |
| 5,476,471 A | 12/1995 | Shifrin et al. | |
| 5,556,414 A | 9/1996 | Turi | |
| 5,584,876 A | 12/1996 | Bruchman | |
| 5,634,895 A | 6/1997 | Igo et al. | |
| 5,645,581 A | 7/1997 | Zurbrugg | |
| 5,681,278 A | 10/1997 | Igo et al. | |
| 5,876,356 A | 3/1999 | Viera et al. | |
| 6,015,422 A | 1/2000 | Kerr | |
| 6,102,918 A | 8/2000 | Kerr | |
| 6,136,022 A | 10/2000 | Nunez et al. | |
| 6,168,620 B1 | 1/2001 | Kerr | |
| 6,187,038 B1 | 2/2001 | Sullivan et al. | |
| 6,250,193 B1 | 6/2001 | Head | |
| 7,060,022 B2 | 6/2006 | Chen et al. | |
| 7,069,835 B2 | 7/2006 | Nishri et al. | |
| 7,083,644 B1 | 8/2006 | Moroni | |
| 7,093,527 B2 | 8/2006 | Rapaport et al. | |
| 7,163,546 B2 * | 1/2007 | Mirizzi | A61B 17/00008 606/159 |
| 7,211,109 B2 | 5/2007 | Thompson | |
| 7,223,286 B2 | 5/2007 | Wright | |
| 7,275,471 B2 | 10/2007 | Nishri et al. | |
| 7,318,835 B2 | 1/2008 | Berra | |
| 7,329,276 B2 | 2/2008 | Smith | |
| 7,455,739 B2 | 11/2008 | Zhou | |
| 7,666,222 B2 | 2/2010 | Wright et al. | |
| 8,172,746 B2 | 5/2012 | Zilla et al. | |
| 8,382,814 B2 | 2/2013 | Zilla et al. | |
| 8,388,616 B2 | 3/2013 | Vogel et al. | |
| 2002/0087176 A1 | 7/2002 | Greenhalgh | |
| 2003/0125789 A1 | 7/2003 | Ross et al. | |
| 2003/0135265 A1 | 7/2003 | Stinson | |
| 2003/0191518 A1 | 10/2003 | Spiridigliozzi et al. | |
| 2004/0102837 A1 | 5/2004 | Boyle et al. | |
| 2004/0158316 A1 | 8/2004 | Jonkman et al. | |
| 2004/0162606 A1 | 8/2004 | Thompson | |
| 2004/0167605 A1 | 8/2004 | Elliott | |
| 2004/0215309 A1 | 10/2004 | Moritz et al. | |
| 2005/0055082 A1 | 3/2005 | Ben Muvhar et al. | |
| 2005/0131520 A1 | 6/2005 | Zilla et al. | |
| 2005/0261780 A1 | 11/2005 | Heino et al. | |
| 2006/0149348 A1 | 7/2006 | Vogel et al. | |
| 2007/0207186 A1 | 9/2007 | Scanlon et al. | |
| 2007/0293932 A1 * | 12/2007 | Zilla | A61F 2/06 623/1.11 |
| 2008/0114391 A1 | 5/2008 | Dieck et al. | |
| 2008/0208323 A1 | 8/2008 | El-kurdi et al. | |
| 2008/0300451 A1 * | 12/2008 | Beck | A61B 17/11 600/36 |
| 2009/0005857 A1 | 1/2009 | Ischinger | |
| 2009/0138065 A1 | 5/2009 | Zhang et al. | |
| 2009/0306764 A1 | 12/2009 | Zilla et al. | |
| 2011/0077729 A1 | 3/2011 | Gross et al. | |
| 2011/0295157 A1 | 12/2011 | Zilla et al. | |
| 2012/0116495 A1 | 5/2012 | Zilla et al. | |
| 2013/0085564 A1 | 4/2013 | Papp et al. | |
| 2013/0123902 A1 | 5/2013 | Iancea et al. | |
| 2013/0144374 A1 | 6/2013 | Zilla et al. | |
| 2014/0046432 A1 | 2/2014 | Orion et al. | |
| 2014/0052234 A1 | 2/2014 | Winshtein et al. | |

FOREIGN PATENT DOCUMENTS

| | | |
|---|---|---|
| JP | 08-509406 A | 10/1996 |
| JP | 2001-500033 A1 | 2/1998 |
| JP | 2003-024453 A | 1/2003 |
| JP | 2006-507092 A1 | 5/2004 |
| JP | 2004-535896 A1 | 10/2004 |
| JP | 2010-508971 A2 | 10/2008 |
| WO | 1995/03010 A1 | 2/1995 |
| WO | WO 95/15130 | 6/1995 |
| WO | 1997/033532 A2 | 9/1997 |
| WO | 9807399 A1 | 2/1998 |
| WO | 1999/56667 A1 | 11/1999 |
| WO | 2000/53121 A1 | 9/2000 |
| WO | 2001/026707 A2 | 4/2001 |
| WO | 2002/098325 A2 | 12/2002 |
| WO | 2003/011190 A2 | 2/2003 |
| WO | 2004/026178 A2 | 4/2004 |
| WO | 2004/047613 A2 | 6/2004 |
| WO | WO 2004/096095 | 11/2004 |
| WO | 2005/044142 A2 | 2/2006 |
| WO | 2006/018268 A2 | 2/2006 |
| WO | 2006/054968 A1 | 5/2006 |
| WO | 2006/072934 A2 | 7/2006 |
| WO | 2006/082574 A2 | 8/2006 |
| WO | 2007/140564 A2 | 12/2007 |
| WO | 2008/070996 A1 | 6/2008 |
| WO | 2008/120184 A2 | 10/2008 |
| WO | 2008/125842 A1 | 10/2008 |
| WO | 2008130387 A2 | 10/2008 |
| WO | 2008/150878 A1 | 12/2008 |
| WO | 2009/043026 A2 | 4/2009 |
| WO | 2010/058406 A1 | 5/2010 |
| WO | WO 2010/058406 | 5/2010 |
| WO | 2012/143922 A1 | 10/2012 |
| WO | 2012/143925 A1 | 10/2012 |
| WO | WO 2012/143922 | 10/2012 |
| WO | WO 2012/143925 | 10/2012 |

OTHER PUBLICATIONS

International Search Report and the Written Opinion dated Aug. 3, 2012 From the International Searching Authority Re. Application No. PCT/IL2012/050121.

Mar. 9, 2010 International Search Report for International Patent Application PCT/IL2009/001105.

* cited by examiner

DEVICES AND METHODS FOR DEPLOYING IMPLANTABLE SLEEVES OVER BLOOD VESSELS

RELATED APPLICATIONS

This application is a National Phase of PCT Patent Application No. PCT/IL2012/050139 having International filing date of Apr. 17, 2012, which claims the benefit of priority under 35 USC § 119(e) of U.S. Provisional Patent Application No. 61/476,347 filed on Apr. 18, 2011. The contents of the above applications are incorporated herein by reference in their entirety, as if fully set forth herein.

FIELD AND BACKGROUND OF THE INVENTION

The present invention, in some embodiments thereof, relates to mechanical supports for bodily vessels, and in particular to devices and methods for deploying implantable sleeves over blood vessels such as peripheral or coronary arterial bypasses grafts.

Coronary heart disease is the leading cause of death in the U.S today. The treatment of choice for patients who suffer from severe coronary artery disease is coronary artery bypass grafting (CABG) surgery. In this procedure, bypasses are built around narrowed arteries, using the patient's native harvested vessels, mainly the internal mammary arteries and the greater saphenous veins. Exposure of the vein graft to high arterial radial pressures is a primary cause of intimal/medial hyperplasia (vessel wall concentric thickening), and as a result, of accelerated atherosclerosis and vein graft failure.

Externally supporting the graft with an external device has the potential to reduce wall stress and cyclic stretching of medial and endothelial cells and reduce diameter mismatch between the vein graft and the artery, all of which might be expected to reduce wall thickening. The efficacy of external support to the graft has been studied by several groups over the past few years and the findings from pre-clinical studies demonstrated significant inhibition of neointimal formation, reduction of atherosclerosis plaques and overall graft thickening reduction comparing to non-supported grafts.

Prior publications describing grafts provided with external supports or layers commonly suggest bonding of the external support to selectively cover the graft, optionally by using glue or sutures. Exemplary publications include U.S. Pat. No. 5,755,659 to Zurbrugg and U.S. Pat. No. 7,998,188 to Zilla et al., the disclosures of which are fully incorporated herein by reference. Such grafts may be provided to the medical practitioners readily covered and supported, or that the medical practitioners or their supporting team are instructed to bond the graft and the external support together prior to grafting. The latter scenario may be time consuming and bothersome to the medical team and may derive special training and expertise in materials bonding and preparations so that the finalized artifact will be satisfactory prepared in a timely manner. Using glue and sutures may also damage the grafted vessel tissue or the grafting procedure and compromise graft patency.

SUMMARY OF THE INVENTION

In an aspect of some embodiments there is provided an apparatus, including a sleeve expander capable of covering with an implantable sleeve an exterior of a bodily vessel, along a chosen length thereof, the sleeve expander configured to maintain at least a portion of the implantable sleeve in an expanded size greater than a cross sectional dimension thereof when in apposition to the exterior.

In some embodiments, the apparatus includes an implantable sleeve readily provided at least partially in the expanded size by the sleeve expander. Optionally, the implantable sleeve includes a meshed portion. Optionally, the meshed portion is braided or knitted. Optionally, the implantable sleeve is shrinkable to fit in diameter to the bodily vessel when having a maximal and a minimal outer diameters in between 3 to 9 mm.

In some embodiments, the portion is extendable from the axially compressed form to an axially extended form. Optionally, the chosen length is 1 cm to 20 cm or is 20 cm to 90 cm.

In some embodiments, the bodily vessel is a native vein or artery or is a graft.

In some embodiments of the invention the apparatus further includes a cutting mechanism configured to cut down the implantable sleeve to a covering length, such as substantially corresponding to the chosen length, when in the apposition to the exterior.

In some embodiments, the sleeve expander includes an internal mandrel enclosing a channel sized to fit over periphery of the bodily vessel, and an external surface having a circumference sized to hold the portion in the expanded size. Optionally, the channel is 4 mm or more in diameter. Optionally, the channel is shorter than the chosen length.

Optionally, alternatively or additionally, the sleeve expander includes at least one leg having a free end detachably connectable to an outer surface of the implantable sleeve, the leg being transferable from a first outward position, in which the portion is in the expanded size, to an inward position, in which the portion is substantially in the cross sectional dimension or is smaller than the cross sectional dimension.

In some embodiments, the cutting mechanism includes a blade and a lever adapted for selectively positioning the blade in a chosen tracked position. Optionally, the blade is rotatable about a longitudinal axis of the implantable sleeve. Optionally, alternatively or additionally, the cutting mechanism includes a laser source and/or a heat source. Optionally, the apparatus includes a switch for selectively altering the cutting mechanism from a non-cutting mode to a cutting mode.

In some embodiments, the cutting mechanism is designed and arranged to cut through a wall of the bodily vessel when readily covered with the implantable sleeve for creating a cut end of the bodily vessel with the implantable sleeve in apposition thereto and flush at the cut end.

In some embodiments, the apparatus includes a bonding agent introducer having an orifice configured to allow flowing of a bonding agent from a reservoir, connectable to the introducer, to an outer periphery of the implantable sleeve, such that the implantable sleeve, when brought in apposition with the bodily vessel, is bondable to the bodily vessel by the bonding agent.

Optionally, alternatively or additionally, the apparatus includes a stitchery apparatus configured to suture a covering section of the implantable sleeve to a corresponding covered section of the bodily vessel.

Optionally, alternatively or additionally, the apparatus includes a pressing apparatus configured to press a covering section of the implantable sleeve and/or a plastically formable fixator provided thereon, such that the covering section is firmly attached to a corresponding covered section of the bodily vessel.

In some embodiments, the apparatus includes metering means arrangeable to facilitate measuring of a covering length of the implantable sleeve upon the bodily vessel.

In an aspect of some other embodiments, there is provided a dispenser including the apparatus and a cover for enclosing the mandrel. Optionally, the dispenser further includes an opening sized and configured to allow the dispensing. In some embodiments, the opening is smaller than the expanded size.

In some embodiments, the dispenser further includes an implantable sleeve readily provided in a preliminary compressed length and extendable up to a maximal preliminary extendable length being substantially longer than the chosen length. Optionally, the preliminary compressed length is 1 cm to 20 cm. Optionally, the preliminary extendable length is 30 cm to 100 cm or is 1 m to 10 m.

In some embodiments, the cutting mechanism is positioned adjacent the opening. Optionally, the cutting mechanism is operated manually or automatically when a covering length of the implantable sleeve portion protrudes through the opening.

In an aspect of some other embodiments, there is provided a tunneling system that includes the apparatus and a lumen extending therein sized for receiving the at least a portion of the implantable sleeve in the expanded size, wherein the tunneling system is capable of tunneling an implantation route for a bodily vessel graft along a subcutaneous path in a limb.

In some embodiments, the tunneling system further includes sharp means shaped and configured to cut through a soft tissue along the path. In some embodiments, the tunneling system further includes tethering means lengthened and configured to pass a vein graft, readily tethetered at a first end thereof, through the lumen.

Optionally, the vein graft is readily anastomosed at a second end thereof.

In an aspect of some other embodiments, there is provided a kit, which includes the apparatus or the dispenser or the tunneling system. In some embodiments, the kit is capable of or configured for placing an implantable sleeve over a chosen length along a bodily vessel and/or providing an implantable sleeve covering for a bodily vessel. In some embodiments, the kit further includes at least one refilling cartridge containing a substituting implantable sleeve.

In an aspect of some other embodiments, there is provided a method that includes at least one of the following steps:
providing the apparatus with the portion of the implantable sleeve readily provided in the expanded size;
passing the bodily vessel in the implantable sleeve; and
releasing the portion to fit over the bodily vessel.

In some embodiments, the method further includes repeating the releasing until covering the covering length. Optionally the method further includes measuring the covering length. Optionally, the method further includes applying the cutting mechanism to cut down the implantable sleeve to the covering length. Optionally, the method is performed ex-vivo or in-vitro.

In an aspect of some other embodiments, there is provided a method that includes at least one of the following steps:
providing an apparatus with the portion of the implantable sleeve readily provided in the expanded size and with a bonding agent reservoir readily connected with the introducer and in direct communication with the orifice;
passing the bodily vessel in the implantable sleeve;
releasing the portion to fit over the bodily vessel;
applying the introducer to allow flowing of a bonding agent from the reservoir through the orifice to an outer periphery of the portion; and
allowing the bonding agent to bond the portion to the bodily vessel.

Optionally, the method further includes applying the cutting mechanism to cut down the implantable sleeve to the chosen length.

In an aspect of some other embodiments, there is provided a method that includes at least one of the following steps:
providing a tunneling system in the subcutaneous tunnel;
passing the blood vessel in the lumen;
releasing the portion to fit over the blood vessel; and
withdrawing the tunneling system from the subcutaneous tunnel.

Optionally, the method further includes maneuvering the tunneling system in the limb along a chosen path to thereby create the subcutaneous tunnel. Optionally, the passing is performed after anastomosing a first end of the blood vessel. Optionally, the method further includes applying the cutting mechanism to cut down the implantable sleeve to the covering length and/or to cut down the blood vessel, after implantable sleeve is in apposition. Optionally, the method further includes anastomosing a second end of the blood vessel after the withdrawing.

In an aspect of some other embodiments, there is provided an apparatus, which includes a sleeve expander capable of covering with an implantable sleeve an exterior of a bodily vessel, along a chosen length thereof, the sleeve expander configured to maintain at least a portion of the implantable sleeve in an expanded size greater than a cross sectional dimension thereof when in apposition to the exterior and external fixating means configured to fixate a covering section of the implantable sleeve to a corresponding covered section of the bodily vessel.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

It is understood that the invention is not limited to the particular methodology, described herein, as these may vary as the skilled artisan will recognize. It is also to be understood that the terminology used herein is used for the purpose of describing particular embodiments only, and is not intended to limit the scope of the invention. It also is be noted that as used herein and in the appended claims, the singular forms "a," "an," and "the" include the plural reference unless the context clearly dictates otherwise.

Unless defined otherwise, all technical and scientific terms used herein have the same meanings as commonly understood by one of ordinary skill in the art to which the invention pertains. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals reference similar parts throughout the several views of the drawings.

Moreover, provided immediately below is a "Definition" section, where certain terms related to the invention are defined specifically. Particular methods, devices, and materials are described, although any methods and materials similar or equivalent to those described herein can be used in the practice or testing of the invention. All references referred to herein are incorporated by reference herein in their entirety.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage.

The term "patient" as in treatment of "a patient" refers to a mammalian individual afflicted with or prone to a condition, disease or disorder as specified herein, and includes both humans and animals.

The term "bodily vessel", unless otherwise defined, refers to blood vessels and grafts, such as veins, arteries and synthetic blood vessels, but may refer also to other elongate internal organs, live or synthetic, configured to function as conduits for fluids or other flowable materials in a patient's body.

The terms "graft" and "grafting" refer to a natural or artificial conduit implantable as replacements to natural bodily vessels in the arm to carry fluids or other flowable materials. In case of blood vessel grafts, the graft is configured to channel blood between two blood vessels or as bypass over an obstructed segment of a single blood vessel, as in the treatment of arterial stenosis, thrombosis or embolus. A graft, according to the present invention, can also be placed as an artificial conduit between an artery and vein of the forearm for use in hemodialysis. Grafts can be used for the aorta (coronary bypass grafts), femoral artery or in the forearm (peripheral bypass grafts). Often, the saphenous vein or left internal thoracic artery are harvested from the patient and used as grafts. PTFE and Dacron are common materials for synthetic vascular grafts.

The term "functional size" in relation to bodily vessels refers to dimensions (e.g., cross sectional dimensions, outer boundary shape, diameters and/or length) when the bodily vessel is provided as part of a living body system and is fully functional in channeling blood or other fluids or flowable materials along its lumen. A bodily vessel not in its functional size will be shrunk and/or compressed, for example when harvested and placed freely outside the body with no external forces applied thereto for increasing its size.

The term "implantable sleeve" refers to any artificial covering sized and configured to be placed in an apposition to a periphery of a bodily vessel and be permanently implanted in a patient's body. Advantageously, though not necessarily, an implantable sleeve may function as an "external support" in which it is prone to change some of the bodily vessel mechanical properties and durability and/or to prevent, lessen and/or positively influence chances of failure, modification and/or tissue modulation thereof, and/or to cast and/or impose a requested shape, size, contour and/or other external boundaries of the bodily vessel. Implantable sleeves may be in the form of a bondable layer, a stent or a sleeve, either full or meshed, either braided, knitted, woven, non-woven, or mechanically machined, and may be made from any materials or elements such as plastics, metals, textiles and others.

The term "apposition" refers to a position being in close proximity, adjacently, in direct contact or in a constricting relation, over, around or juxtaposing, a target surface.

The term "covering length" refers to a length of the implantable sleeve when covering and affixed to a periphery of a bodily vessel being in a functional size. The covering length may be substantially corresponding a chosen length of the bodily vessel which may be equal or smaller its entire length, or optionally be lengthened over the length of a functionally sized bodily vessel for, optionally, covering also the anastomosed areas and/or part of the hosting vessels anastomosed thereto.

The terms "cast", "casting" or "molding" refer to the forming of externally shaped boundaries, optionally three-dimensional, to an externally supported bodily vessel either by constricting and/or changing the vessel shape and/or contour by exerting forces thereto, and/or by restricting its deformation and/or modulation to a specific final shape and/or contour.

The term "braid" or "braiding" refers to a pattern formed by intertwining three or more strands of flexible material, such as wires, threads or yarns, which may be made for example of polymers, textiles or metal (e.g., stainless steel threads).

The term "knit" refers to a needlework created by interlacing yarn in a series of connected loops using straight eyeless needles or by machine.

The following preferred embodiments may be described in the context of exemplary vascular bypass procedures for ease of description and understanding. However, the invention is not limited to the specifically described devices and methods, and may be adapted to various clinical applications without departing from the overall scope of the invention. For example, devices and related methods including concepts described herein may be used for externally supporting grafts and other bodily vessels such as but not limited to: arteries, veins, synthetic grafts, coronary bypass grafts, peripheral bypass grafts, gastrointestinal vessels, and soft and semi-hard tissues.

The present invention, in some embodiments thereof, relates to mechanical supports for bodily vessels, and in particular to devices and methods for deploying implantable sleeves over bodily vessels including blood vessels such as peripheral or coronary arterial bypasses grafts.

In some embodiments of the invention, the implantable sleeve comprises a meshed portion, which may be braided, knitted, woven, or non-woven. Known art describing exemplary implantable meshed sleeves, or grafts readily provided with externally covering meshed sleeves, include: U.S. Pat. No. 3,626,947, U.S. Pat. No. 4,743,251, U.S. Pat. No. 5,755,659, U.S. Pat. No. 6,071,306, U.S. Pat. No. 5,824,047, U.S. Pat. No. 6,358,275, U.S. Pat. No. 8,057,537, U.S. Pat. No. 7,998,188, U.S. patent application Ser. No. 13/130,760 and international patent application number PCT/IL2012/050121; the disclosures of which are fully incorporated herein by reference.

According to some of the above mentioned known arts, the implantable sleeves are worn over the bodily vessels and fixed to a chosen length using external fixation means such as sutures or bonding agents (e.g., glues, adhesives or other curable materials). According to some other known arts, other designs of implantable sleeves may include mechanical features which allow self-fixation to the bodily vessel upon release or manual shaping in a manner that obviates the need for external fixators.

Some of the known implantable sleeves are provided separately to the grafts, so that the medical practitioners need to size and deploy them manually to the graft, either before or during the implantation or grafting in patient's body. After the graft is prepared and cut down to a chosen length may then be covered with the implantable sleeve. In scenarios where the medical practitioner is instructed to support the graft ex-vivo prior to implantation, the graft is commonly in compressed and shrunk form so external means (e.g., saline injectors, internal inflatable devices or others) are needed to extend it to its functional size as when it is implanted and channeling blood in the target host vascular system.

Figure 1A:
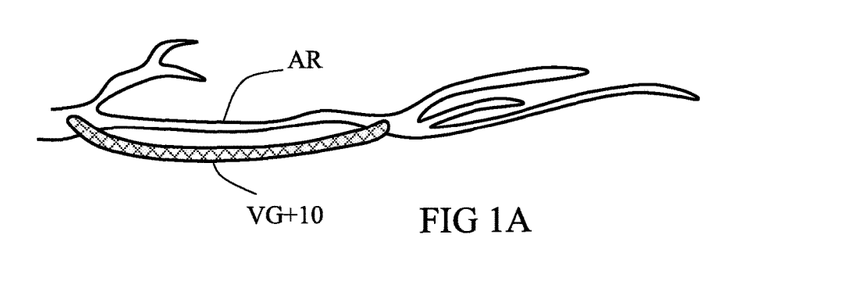
FIGS. 1A-B schematically illustrate side views of a graft anastomosed to an arterial system and externally supported with an implantable sleeve, in accordance with embodiments of the present invention.
Figure 1B:
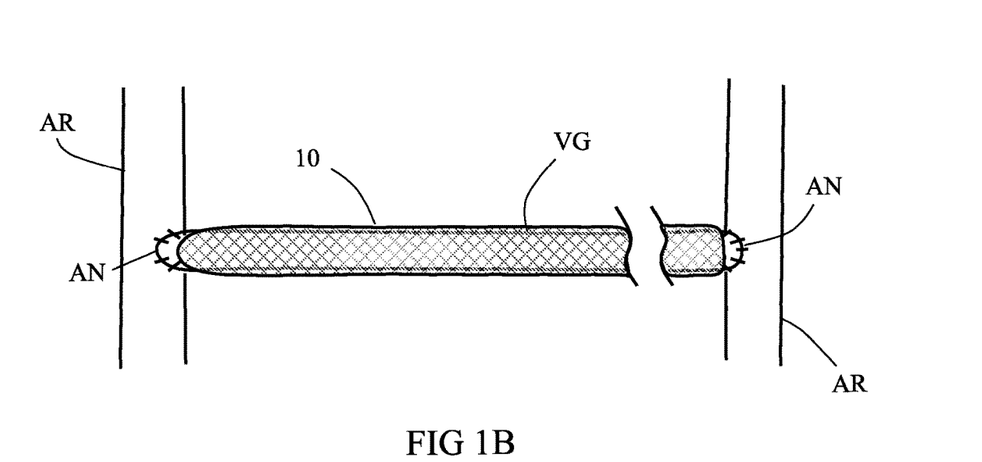

FIGS. 1A-B schematically illustrate side views of a graft VG externally supported with an implantable sleeve 10. Graft VG is shown anastomosed at both ends with anastomoses AN to a hosting vascular system which includes an artery AR. Artery AR may be a coronary or a peripheral vessel. Graft VG may be a naturally harvested graft, for example a saphenous vein graft, or may be a synthetic graft still in need for mechanical modification adjustable with implantable sleeve 10 when in apposition thereto.

Implantable sleeve 10 may be any of the implantable sleeves as described in the known arts listed above, or may include other designs and forms as known to art or are in development. In some embodiments, implantable sleeve 10 is decreaseable from a first expanded size to a covering size when in apposition to graft VG periphery, optionally is shrinkable to fit in diameter. In some embodiments, such an apposition and/or fitting is applicable when graft VG is of a functional size having a maximal and a minimal outer diameters in between 1 mm to 15 mm, or optionally in between 3 mm to 9 mm. Implantable sleeve 10 may be provided in a covering length or cut down to a covering length. Implantable sleeve 10 may be picked up from a variety of implantable sleeves differentiated by size (e.g., length and/or diameter), in correspondence with graft VG size (e.g., functional size) which may vary, for example in case of common vascular bypass surgeries, from about 5 cm to about 20 cm in coronary bypasses, or from about 20 cm to about 90 cm in peripheral bypasses.

Exemplary Delivery Apparatus

In an aspect of some embodiments, there is provided an apparatus for covering with an implantable sleeve, optionally a tubular sleeve, an exterior of a bodily vessel, along a chosen length thereof. In some embodiments of the invention, the apparatus includes a sleeve expander configured to maintain at least a portion of the implantable sleeve in an expanded size greater than a cross sectional dimension thereof when in apposition to the exterior. In some embodiments, the apparatus further comprises a cutting mechanism configured to cut down the implantable sleeve to a covering length, such as substantially corresponding to the chosen length, when in the apposition to the exterior.

Figure 2A:
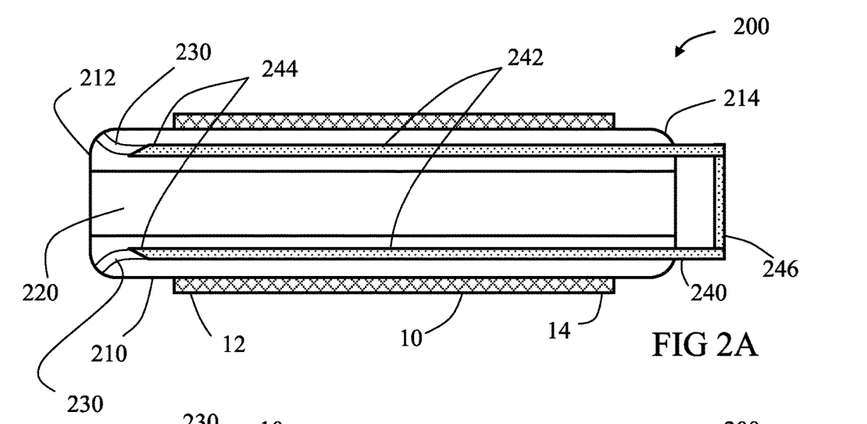
FIGS. 2A-C schematically illustrate cut views at different stages in deploying an implantable sleeve over a bodily vessel using an exemplary delivery apparatus, in accordance with embodiments of the present invention.
Figure 2B:
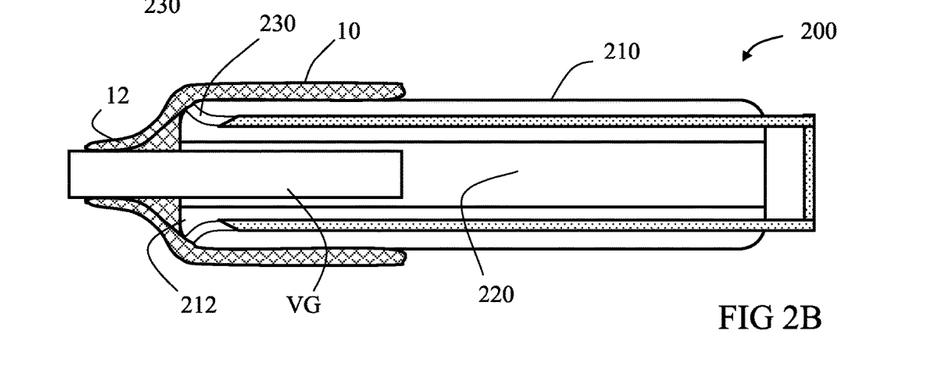
Figure 2C:
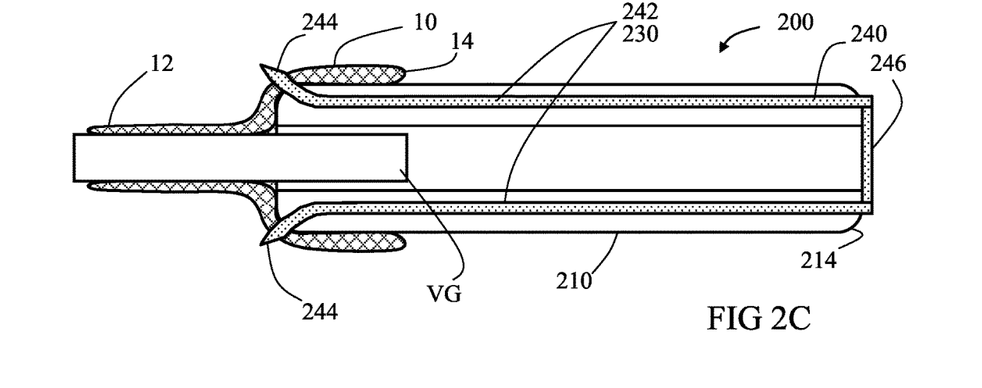

Reference is now made to FIGS. 2A-C which schematically illustrate cut views at different stages in deploying implantable sleeve 10 over graft VG, using an exemplary delivery apparatus 200, in accordance with embodiments of the present invention. Optionally, delivery apparatus 200 consists essentially of biocompatible surgical-grade components and/or materials, optionally plastics and/or metal alloys. Delivery apparatus 200 may be disposable or include disposable, optionally single-use, parts, or it may be essentially applicable for multiple-use.

Delivery apparatus 200 includes a sleeve expander 210, in the form of an internal mandrel, having a distal end 212, a proximal end 214 and enclosing a channel 220 sized to fit over periphery of graft VG. In some embodiments, channel 220 is 2 mm or more, optionally 4 mm or more, optionally 6 mm or more in diameter. In some embodiments, channel 220 is shorter than graft VG length, optionally shorter than a chosen length thereof and/or a covering length substantially corresponding that chosen length. Sleeve expander 210 further includes an external surface having a circumference sized to hold implantable sleeve 10, or at least a portion thereof, in an expanded size being substantially greater than periphery of graft VG or even of channel 220 diameter. In some embodiments, the circumference of sleeve expander 210 is selectively changeable to expand implantable sleeve 10 or a portion thereof to the expanded size. Optionally, sleeve expander 210 is expandable in diameter, optionally inflatable.

Delivery apparatus 200 includes tracks 230 provided along its length and comprising proximal and distal openings, tracks 230 being generally straight but optionally curved adjacent distal end 212, optionally outwardly curved towards sleeve expander 210 periphery (as shown in FIG. 2A). Cutting mechanism 240 is provided slidably movable in tracks 230 from a withdrawn position (as shown in FIGS. 2A and 2B) to a deployed position where it is applicable to cut down a partly taken off implantable sleeve 10, optionally readily covering part of graft VG (as shown in FIG. 2C). Cutting mechanism 240 includes a plurality (or only one—not shown) of arms 242 connected at their proximal ends with a manually operable button 246. Arms 242 are optionally elastic or semi-rigid to take the form of non-straight segments of tracks 230. Arms 242 end with or connected to blades 244 at their distal ends. In some embodiments, arms 242 and/or button 246 may serve as a lever if tracks 230 are at least partially curved or otherwise non-straight and when blades 244 are selectively positioned in a chosen tracked position, for example, when are pushed distally to protrude outwardly from sleeve expander 210 circumference. In some embodiments, cutting mechanism 240 is a differential cutting mechanism configured to cut only non-elastic members therefore avoiding cutting healthy elastic blood vessels such as graft VG. For example, each blade 244 is connected to an arm 242 with a preloaded spring (not shown) designed to collapse only over a threshold compression force smaller than a force known to dissect graft VG. In some embodiments of the invention, cutting mechanism 240 and/or blades 244 are rotatable about a longitudinal axis of implantable sleeve 10 and/or of graft VG so that cutting down of implantable sleeve 10 is applicable when blades 244 are first move into outward position and then sleeve expander 210 is revolving. In such a case, blades 244 are sharp in at least one of their lateral sides so that cutting is made at rotational motion thereof.

As shown in FIG. 2A, implantable sleeve 10 may be readily provided at least partially in said expanded size said sleeve expander 210. Safety mechanism (not shown) may be used to withhold button 246 from shifting unintentionally from withdrawn position. A shown in FIG. 2B, graft VG is introducible, at least partly, into channel 220 and a medical practitioner may manually introduce it therein while keeping a distal portion outside. Graft VG may be provided readily in functional size, optionally inflated to approximately that functional size. Implantable sleeve 10 may then be partially pulled distally so that its distal end 12 is lessened in size and brought into apposition with graft VG exterior. Distal end 12 may be fixated to graft VG, for example by gluing, suturing, crimping and/or by compressing an external fixator thereupon (not shown). As shown in FIG. 2C, implantable sleeve 10 together with graft VG is further withdrawn distally until a desired covering length of the graft VG is met. Button 246 may then be pushed to protrude blades 244 outwardly from tracks 230 and through implantable sleeve 10 from the inside-out. Revolving of sleeve expander 210 about its axis will circumferentially cut implantable sleeve 10 down to a desired covering length. After cutting down in length, a proximal portion 14 of implantable sleeve 10 remains provided in expanded size over sleeve expander 210. Remaining proximal portion 14 may serve for an additional covering of bodily vessels or can be discarded with or without sleeve expander 210.

In some embodiments, delivery apparatus 200 is provided as part of a kit further including at least one refilling cartridge (not shown) containing at least one implantable sleeve substituting to implantable sleeve 10.

In an aspect of some embodiments, there is provided a method of covering a chosen length of a bodily vessel, such as graft VG, with an implantable sleeve, such as implantable sleeve 10, the method comprising: providing an apparatus, such as delivery apparatus 200, having at least proximal portion 14 readily provided in expanded size; passing the bodily vessel within the implantable sleeve; and releasing the distal portions, such as distal portion 12, of the implantable sleeve to fit over the bodily vessel. Optionally, releasing of implantable sleeve distal portions is repeated until covering the bodily vessel along a desired covering length. Optionally, before or after release the covering length is measured. A cutting mechanism, such as cutting mechanism 240, may then be applied to cut down the implantable sleeve to the desired covering length. The method may be performed in vitro (i.e., outside patient's body). Optionally and alternatively, a first end of graft VG is first anastomosed to a first host location (not shown) and only then its covering with implantable sleeve 10 begins.

Exemplary Delivery Apparatuses Comprising External Fixating Means

Figure 3:
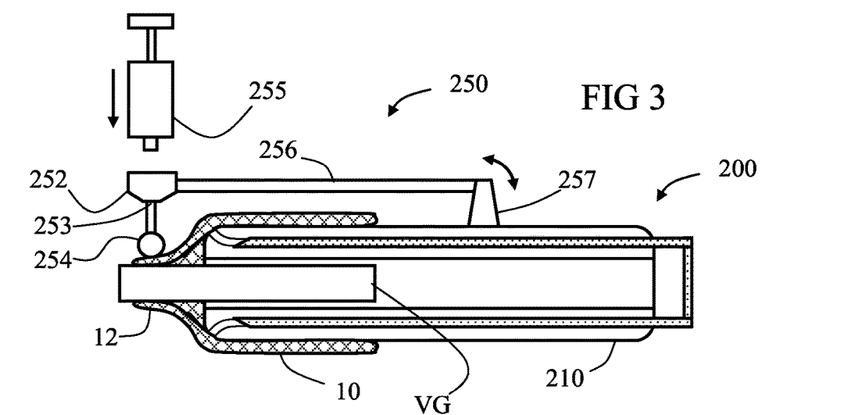
FIG. 3 schematically illustrates a cut view of an exemplary delivery apparatus comprising means to bond an implantable sleeve onto periphery of a bodily vessel, in accordance with embodiments of the present invention.

Reference is made to FIG. 3 which schematically illustrates a cut view of exemplary delivery apparatus 200 further comprising means 250 to bond implantable sleeve 10 onto periphery of graft VG, in accordance with some embodiments of the present invention. Means 250 includes a bonding agent introducer 252 having an orifice 253 configured to allow flowing of a bonding agent from a reservoir 255, connectable to introducer 252, to an outer periphery implantable sleeve, such that when implantable sleeve 10 is brought in apposition with said graft VG, it is bondable to graft VG by the bonding agent. Introducer 252 is connected to an arm 256 extending over at least partially along a length of sleeve expander 210 and connected thereto with an extension 257. Extension 257 may be detachably connected or permanently connected to sleeve expander 210. Arm 256 may be pivotally movable with respect to extension 257 thereby allowing operation of delivery apparatus 200 with easy handling and/or with different dimensions of the implantable sleeves. Introducer 252 may be provided with a roller 254, optionally porous, which enables smooth delivery of bonding agent over the covering portion of implantable sleeve 10 while revolving over the implantable sleeve and, optionally, continuously delivering the bonding agent thereto while implantable sleeve 10 and graft VG are distally withdrawn with respect to delivery apparatus 200.

A method of covering a chosen length of a bodily vessel with an implantable sleeve, such as implantable sleeve 10, may include: providing an apparatus, such as delivery apparatus 200 connected with means 250, with at least a portion of the implantable sleeve being readily provided in an expanded size and with a bonding agent reservoir, such as reservoir 255, readily connected with a bonding agent introducer, such as introducer 252, and in direct communication with an orifice, such as orifice 253; passing a bodily vessel, such as graft VG, within the implantable sleeve; releasing the portion of the implantable sleeve to fit over the bodily vessel; applying the bonding agent introducer to allow flowing of a bonding agent from the reservoir through the orifice to an outer periphery of the implantable sleeve portion; and allowing the bonding agent to bond the implantable sleeve portion to the bodily vessel. The method may further include applying a cutting mechanism to cut down the implantable sleeve to a chosen length.

Figure 4:
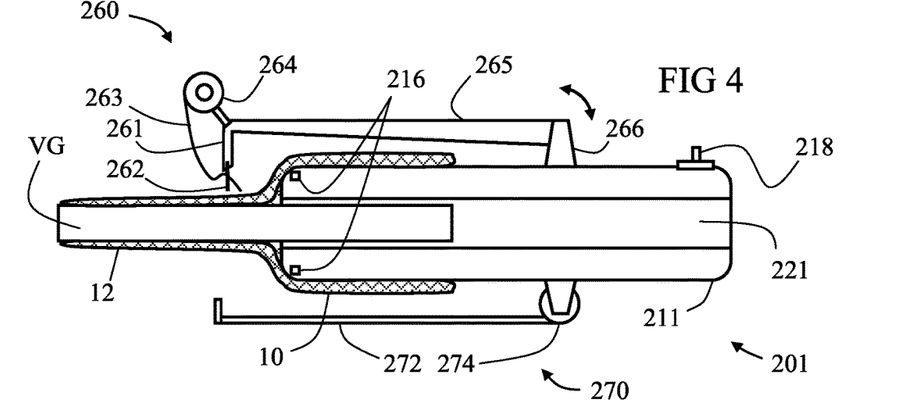
FIG. 4 schematically illustrates a cut view of an exemplary delivery apparatus comprising means to suture an implantable sleeve onto periphery of a bodily vessel, in accordance with embodiments of the present invention.

FIG. 4 schematically illustrates a cut view of a delivery apparatus 201 which comprises means 260 to suture implantable sleeve 10 onto periphery of graft VG, in accordance with different embodiments of the present invention. Delivery apparatus 201 may be similar in dimensions to delivery apparatus 200 including a sleeve expander 211 which comprises a channel 221 for passing bodily vessels therethrough and a cutting mechanism incorporating heat sources 216, optionally light or laser sources. A switch 218 is present for selectively altering the cutting mechanism from a non-cutting mode to a cutting mode. Means 260 includes a stitchery apparatus 261 configured to suture a covering section of implantable sleeve 10 to a corresponding covered section graft VG. Stitchery apparatus 261 includes a needle 262 and a thread 263 combination that are mechanically arranged to stitch, sew, suture and/or anastomose according to pre-setting. Thread 263 is shown provided in a bobbin 264 connected to stitchery apparatus 261. Stitchery apparatus 261 is connected to an arm 265 extending over at least partially along a length of sleeve expander 211 and connected thereto with an extension 266. Extension 266 may be detachably connected or permanently connected to sleeve expander 211. Arm 265 may be pivotally movable with respect to extension 266 thereby allowing operation of delivery apparatus 201 with easy handling and/or with different dimensions of the implantable sleeves.

Delivery apparatus 201 is shown further comprising metering means 270 arrangeable to facilitate measuring of a covering length of implantable sleeve 10 upon graft VG. Metering means 270 may be a measuring tape type comprising a strip 272, optionally a metal self-retracting strip with linear-measurement markings, provided in a roller 274.

Figure 5:
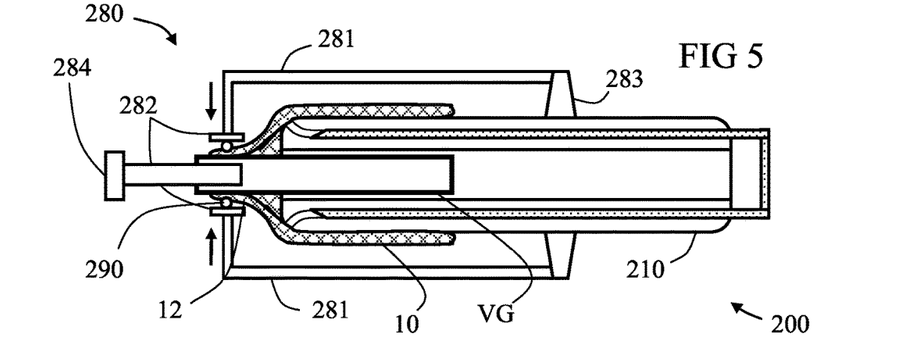
FIG. 5 schematically illustrates a cut view of an exemplary delivery apparatus comprising pressing means to fixate an implantable sleeve to a periphery of a bodily vessel, in accordance with embodiments of the present invention.

FIG. 5 schematically illustrates a cut view of delivery apparatus 200 further comprising pressing means 280 for fixating implantable sleeve 10 to periphery of graft VG, in accordance with different embodiments of the present invention. Pressing means 280 comprises a pressing apparatus 282 configured to press a covering section of implantable sleeve 10 and a plastically formable fixator 290 provided thereon, such that the covering section is firmly attached to a corresponding covered section of graft VG. Fixator 290 may be in the form of a ring or any other encircling shape and yieldable under pressing forces applied by pressing apparatus 282 to plastically deform into a non-re-expandable pressed form. A tubular insert 284 may be provided in graft VG lumen being rigid enough to oppose compressing forces of pressing apparatus 282 so that fixator 290 is bound from narrowing graft VG lumen to under a minimally allowed diameter. After fixator 290 pressing, insert 284 may be removed. Pressing apparatus 282 is connected with levers 281, each is pivotally movable about an extension 283 connected, optionally detachably connected, to sleeve expander 210.

Optionally and alternatively, a different insert (not shown), rather than insert 284, is used, and having a lumen passing therethrough being sized to and capable of accommodating distal portion of graft VG and act as a circumferential mechanical barrier between exterior of graft VG and interior of distal portion 12 of implantable sleeve 10. Optionally, alternatively or additionally, fixator 290 may not be present or may be used a pressing apparatus for crimping down a yieldable bundle of threads and/or layer, and after pressing optionally be removed.

Exemplary Delivery Apparatus Comprising Sleeve Extending Legs

Figure 6A:
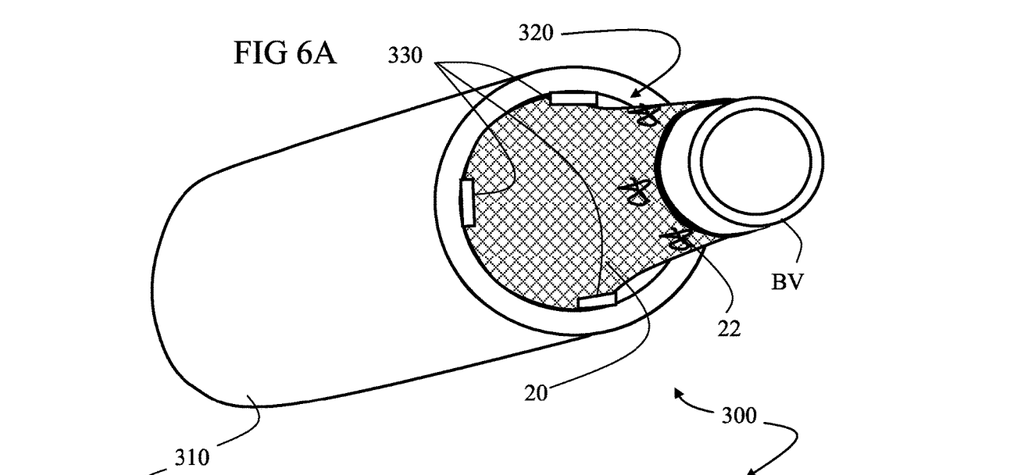
FIGS. 6A-B schematically illustrate isometric views at different stages in deploying an implantable sleeve over a bodily vessel using an exemplary delivery apparatus which comprises sleeve extending legs, in accordance with embodiments of the present invention.
Figure 6B:
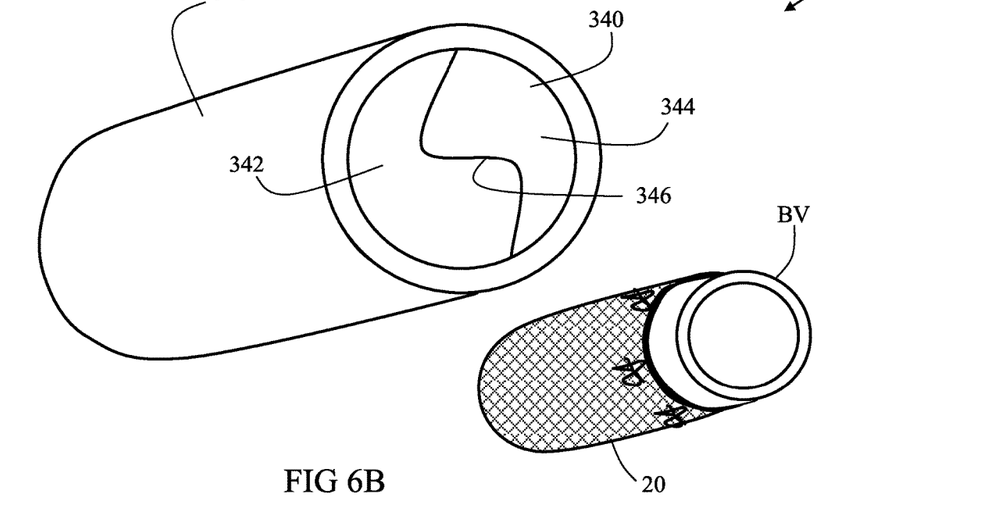

Reference is now made to FIGS. 6A-B which schematically illustrate isometric views at different stages in deploying an implantable sleeve 20 over a bodily vessel BV using an exemplary delivery apparatus 300 which comprises sleeve extending legs 330, in accordance with embodiments of the present invention. Implantable sleeve 20 may be similar or different than implantable sleeve 10 and/or may be any of the implantable sleeves as described in the known arts listed above, or may include other designs and forms as known to art or are in development.

Delivery apparatus 300 includes a tubular body 310 and a channel 320 passing therethrough and sized to accommodate a bodily vessel BV and at least a portion of implantable sleeve 20 in an expended size. Each leg 330 has a free end detachably connectable to an outer surface of implantable sleeve 20 (shown connected to implantable sleeve in FIG. 6). Optionally (not shown), legs 330 are transferable from a first outward position, in which a portion of the implantable sleeve 20 is in an expanded size, to an inward position (not shown), in which same portion is substantially equal to or smaller than cross sectional dimension of the implantable sleeve when in apposition to the exterior of bodily vessel BV.

In FIG. 6A, delivery apparatus 300 is shown in a deployment stage, where bodily vessel BV is partly accommodated in channel 320 and partly protruded distally out of it. Implantable sleeve 20 is sutured at its distal end, using a plurality of stitches 22, to bodily vessel BV. When bodily vessel BV is distally withdrawn away from lumen 320, other portions of implantable sleeve 20 are also withdrawn and revealed from within lumen 320. In some embodiments, implantable sleeve 20 is self-compressible and/or shrinking-to-fit so that the revealed portions immediately compressed into apposition with respect to bodily vessel BV exterior. Optionally and alternatively, implantable sleeve is looser so that external fixating means (e.g., bonding or suturing) are needed to apposably fit an entire covering length over bodily vessel BV.

A cutting mechanism 340 provided with delivery apparatus 300 is shown in-action in FIG. 6B. In some embodiments, cutting mechanism 340 is a guillotine or iris type cutter comprising a plurality of cutting blades, such as blades 342 and 344, shiftable from a circumferentially outward position to an inward intersection position, characterized with a cutting intersection line 346. Cutting mechanism 340 is designed and arranged to cut through a wall of bodily vessel BV when readily covered with implantable sleeve 20 for creating a cut end of bodily vessel BV with the implantable sleeve in apposition thereto and flush at the cut end, as shown in FIG. 6B.

Exemplary Dispenser for Dispensing an Implantable Sleeve

In an aspect of some other embodiments, there is provided a dispenser for dispensing a portion of an implantable sleeve over a chosen length along a graft, the dispenser comprising an apparatus, such as delivery apparatus 200, sleeve expander 210, delivery apparatus 201, sleeve expander 211 or delivery apparatus 300; and a cover for enclosing a sleeve expander or mandrel, the cover comprising an opening sized and configured to allow dispensing. Optionally the opening is smaller than the expanded size, optionally substantially the size of an implantable sleeve covering section in apposition to an exterior of the graft.

In some embodiments, the dispenser further comprises an implantable sleeve. Optionally, the implantable sleeve is readily provided in a preliminary compressed length and is extendable up to a maximal preliminary extendable length being substantially longer than the chosen length along the graft. In some embodiments, the preliminary compressed length is 1 cm to 20 cm. In some embodiments, the preliminary extendable length is 30 cm to 100 cm. Optionally and alternatively, the preliminary extendable length is 1 m to 10 m.

In some embodiments of the invention, a cutting mechanism is positioned adjacent the cover opening. Optionally, the cutting mechanism is operated manually or automatically when a desired covering length of the implantable sleeve portion protrudes through said opening.

Figures 7A, 7B:
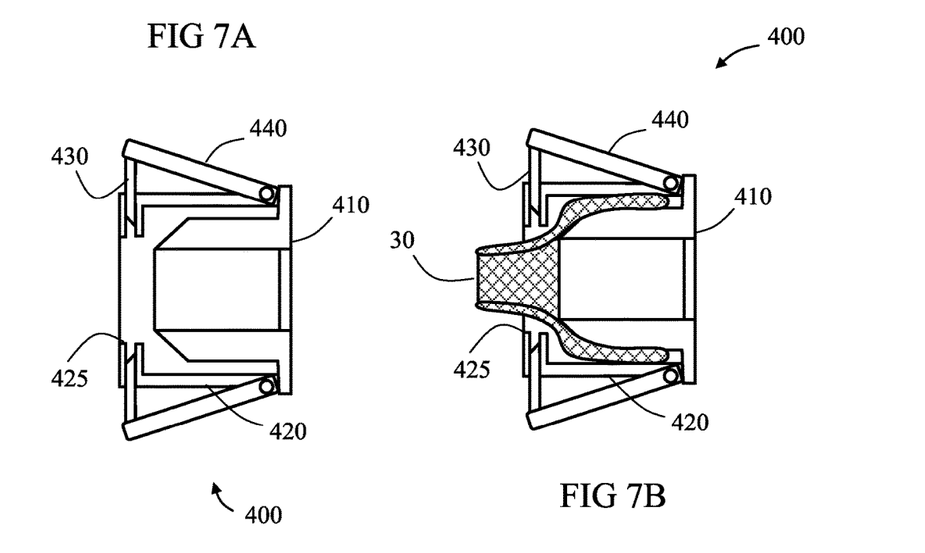
FIGS. 7A-C schematically illustrate cut views of an exemplary dispenser for dispensing implantable sleeve along a chosen length of a blood vessel, in accordance with embodiments of the present invention.
Figure 7C:
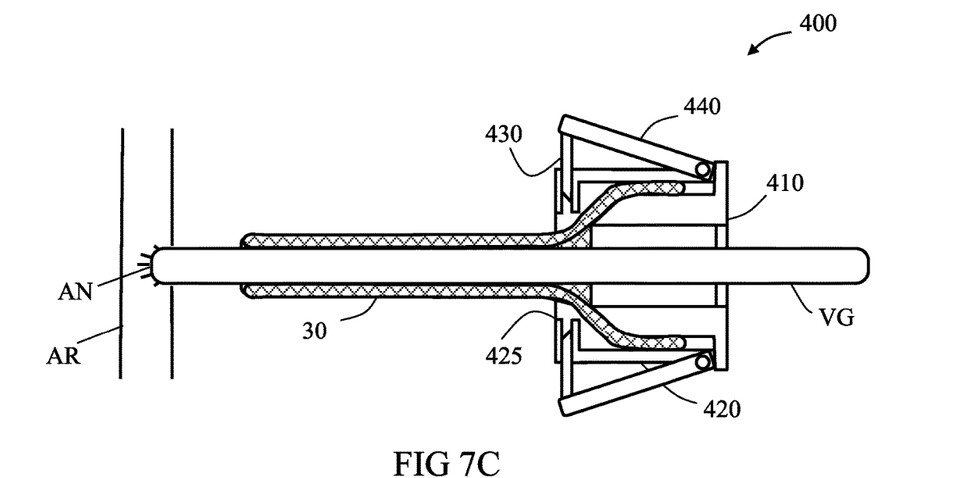

Reference is now made to FIGS. 7A-C which schematically illustrate cut views of an exemplary dispenser 400 for dispensing an implantable sleeve 30 along a chosen length of a graft VG, in accordance with embodiments of the present invention. Implantable sleeve 30 may be similar or different than any of implantable sleeves 10 and 20, and/or may be any of the implantable sleeves as described in the known arts listed above, or may include other designs and forms as known to art or are in development.

In some embodiments, dispenser 400 includes an internal mandrel 410 having a first end and a second end with a channel therebetween, sized to fit over a maximal diameter of graft VG, and an external surface sized to hold implantable sleeve 30 in an axially compressed form. In some embodiments, dispenser 400 further includes a cover 420 for enclosing internal mandrel 410, which includes an opening 425 that is sized and configured to allow said dispensing of a distal portion of implantable sleeve 30 along graft VG. In some embodiments, cutting means 430 are provided for cutting a requested length or portion of implantable sleeve 30 according to need and/or when graft VG is completely covered. In some embodiments, cutting means 430 include a sharp instrument, such as a guillotine, a punch-cut, a v-cut or any other possible cutter, optionally concentric cutter similar to cigars cutter. In some embodiments, the sharp instrument which is capable of cutting or dissecting implantable sleeve 30 protrudes through opening 425 from the compressed portion reserved in dispenser 400. In some embodiments, the sharp instrument, when operated, travels radially inwardly until adjacent external surface of graft VG. Alternatively and optionally, the sharp instrument travels in an angle inwardly into a hidden slot in cover 420 and/or mandrel 410 and/or moves in a longitudinal or other direction instead (not shown). Optionally, this maneuver facilitates cutting of implantable sleeve 30, but alternatively the operator may rotate dispenser 400 or only cutting means 430 around implantable sleeve 30 and graft VG to achieve a requested cutting result.

In some embodiments, cutting means 430 are operated manually by using lever 440 hingedly connected to cover 420. Alternatively and optionally, cutting means 430 are operated automatically, for example by using a sensor based circuit or other means known to art (not shown), when a desired covering length of implantable sleeve 30 protrudes. In some embodiments (not shown), dispenser 400 and/or any of its parts may be disassembled or cut sagittally (i.e., along its length) and/or may include cutting means (same or different than cutting means 430) which may cut the compressed portion of implantable sleeve along its length. Last exemplary embodiment may be useful in cases where the dispenser is applied after both ends of graft VG are anastomosed to the vascular system and the dispenser is to be removed after covering the graft.

The following exemplary steps may take place when using dispenser 400 to deploy a portion of implantable sleeve along a chosen length of graft VG. After graft VG is anastomosed with anastomosis AN at its distal end to artery AR (as shown in FIG. 7C), dispenser 400 preloaded with a bundle of implantable sleeve, is placed over it. Dispenser 400 is preloaded by deploying implantable sleeve in a compressed and radially extended fashion over internal mandrel 410 and then capping it with cover 420. The operator may then pull out a small portion of implantable sleeve 30 and fixed it with his fingers or with external fixating means to distal end of graft VG, and then pull proximally dispenser 400 while releasing further portions of implantable sleeve 30 along the graft. In some embodiments, implantable sleeve decreases in diameter, when extended, to a smaller diameter in apposition to exterior of graft VG, optionally substantially similar or optionally slightly greater than graft VG cross sectional dimensions. Optionally, implantable sleeve, when extended, shrinks to fit to any diameter between 3 to 9 mm. In some embodiments, the operator may then cut and disconnect the requested portion of implantable sleeve and remove dispenser 400. In some embodiments, the operator may use cutting means 430 to cut through implantable sleeve 30 as well as through graft VG. In some embodiments, dispenser 400 includes other means to disperse glue on top of the dispensed portion of external support 4100 to fasten it to the covered graft VG.

Exemplary Delivery Tunnelers

A common practice for introducing grafts in peripheral arterial systems, for example in legs, is atraumatic or less traumatic implantation of percutaneous grafts using a tunneling system, also referred to as a tunneler. A tunneler is used to create a continuous subcutaneous passage along a chosen length of an ill artery portion and then to allow a passing through its lumen (using tethering means such as a dedicated hook wire or elongated grasping forceps), when extending percutaneously, the graft for final grafting and implantation.

Figure 8A:
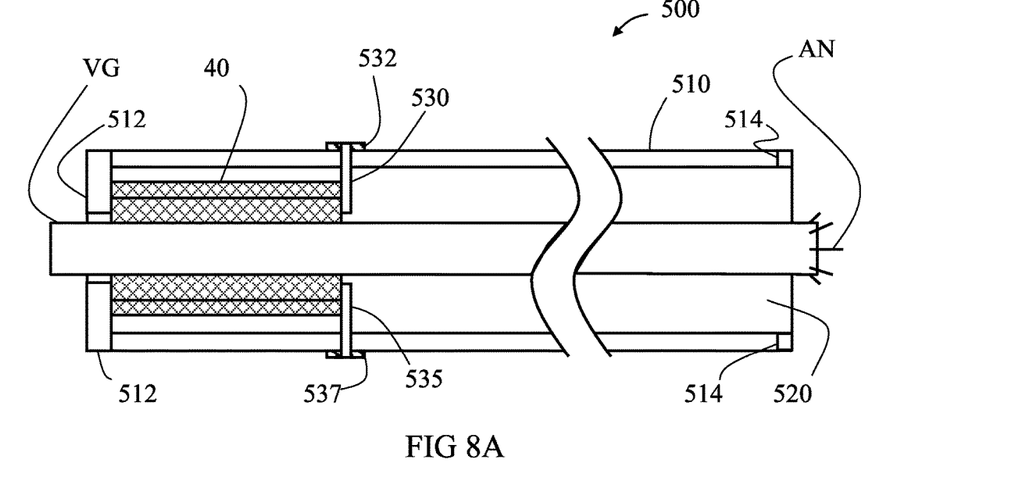
FIGS. 8A-B schematically illustrate cut views at different stages in deploying a self-extending type implantable sleeve onto a vein graft using an exemplary delivery tunneler, in accordance with embodiments of the present invention.
Figure 8B:
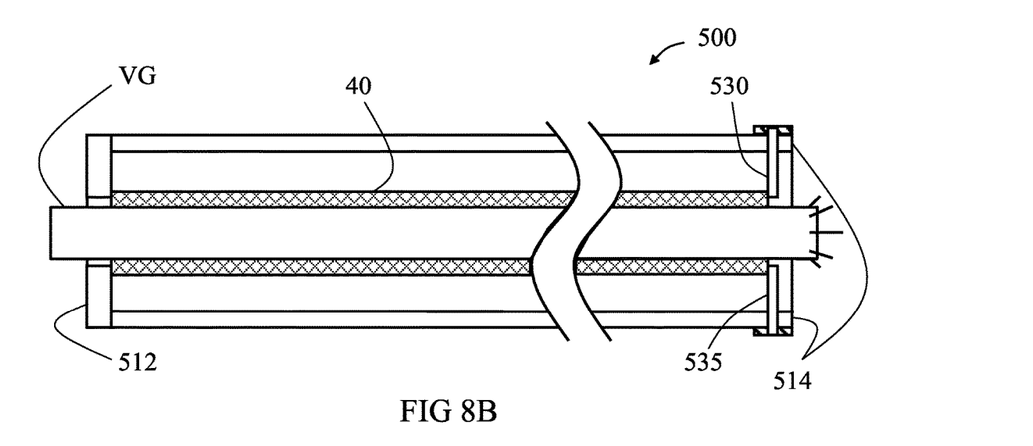

Reference is made to FIGS. 8A-B which schematically illustrate cut views at different stages in deploying a self-extending type implantable sleeve 40 onto a vein graft VG using an exemplary delivery tunneler 500, in accordance with embodiments of the present invention. In contrary to the use of known tunneling systems, tunneler 500 is designed and configured to deploy an implantable sleeve, such as implantable sleeve 40, and cover a bare vein graft VG, optionally readily anastomosed at one end by anastomosis AN. Implantable sleeve 40 may be similar or different than any of implantable sleeves 10, 20 and 30, and/or may be any of the implantable sleeves as described in the known arts listed above, or may include other designs and forms as known to art or are in development. In some embodiments, implantable sleeve 40 is a self-extending and/or self-compressing meshed sleeve, optionally a braided sleeve comprising spring wires intertwined in low braiding angles when in a relaxed length.

Figure 9A:
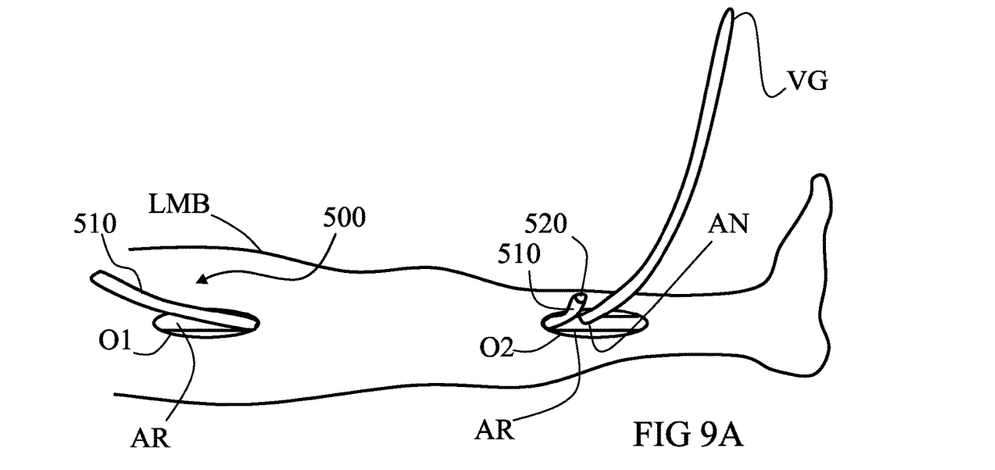
FIGS. 9A-C schematically illustrate side views at different stages in implanting a vein graft in a limb and deploying an implantable sleeve thereupon using a delivery tunneler, in accordance with embodiments of the present invention.
Figure 9B:
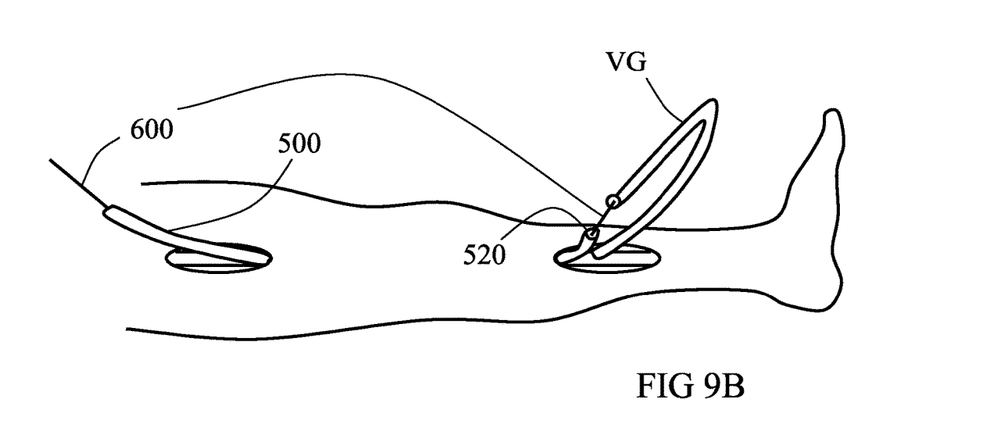

As preliminary steps (as shown in FIG. 9A), delivery tunneler 500 may be first provided subcutaneously between a proximal opening O1 and a distal opening O2 made to a limb LMB exposing two portions of an ill artery AR; and vein graft VG may then be passed via a lumen 520 thereof across its length (using tethering means 600) from distal to proximal side (as shown in FIG. 9B). Delivery tunneler 500 includes an elongated body 510 housing lumen 520 along its entire length. Body 510 may be made from any material or components known to art, for example from plastic or stainless steel.

Figure 9C:
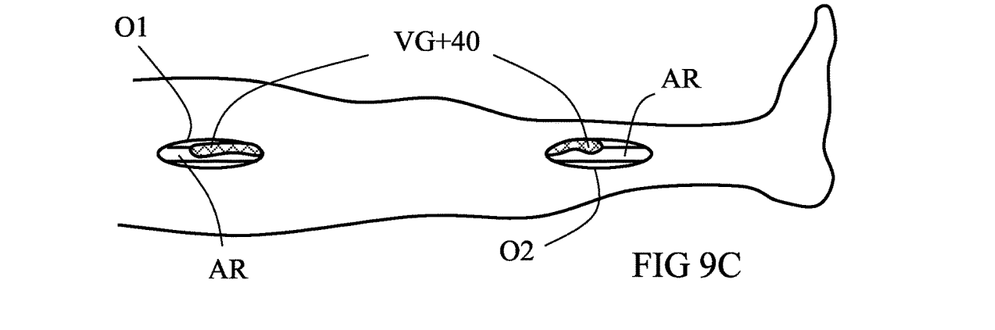

Lumen 520 is wide at least to the extent to allow implantable sleeve 40 to be held compressed and forced to a wide diameter than in its relaxed length, the wider diameter allows easy passing over outer periphery of vein graft VG. Implantable sleeve 40, as shown in FIG. 8A, is cocked between a proximal static stopper 512, allowing only passage of smaller diameter graft VG passing through an inner diameter thereof, and slidable levers 530 and 535, capable of sliding using sliders 532 and 537, respectively, through slitted tracks provided between proximal stopper 512 and distal stopper 514. Positioning of levers 530 and 535 relative to proximal stopper 512 determines the compressed length of implantable sleeve as well as its increased diameter. By sliding levers 530 and 535 towards distal stopper 514, implantable sleeve gradually extends and decreased in diameter until reaching a chosen length or up to a final relaxed length. In FIG. 9C, implantable sleeve 40 is shown at relaxed length when covering most of graft VG length, now being anastomosed at both ends thereof.

Other designs of delivery tunnelers may be used instead (not shown), for example tunnelers to selectively shrink or compress a meshed covering onto a graft. An annular balloon or other inwardly expanding means may be provided in a tunneler lumen to suppress an external covering onto outer periphery of the graft in a homogenous manner. Other or same means may be used to pour or dispense adhesives over the covering and in between the covering and the graft.

In an aspect of some embodiments the is provided a method of covering a chosen length of a blood vessel, such as graft VG, with an implantable sleeve, such as implantable sleeve 40, in a subcutaneous tunnel in a limb, the method comprising: providing a tunneling system, such as tunneler 500, in the subcutaneous tunnel; passing the bodily vessel in its lumen; releasing at least a portion of the implantable sleeve to fit over the blood vessel; and withdrawing the tunneling system from the subcutaneous tunnel. In some embodiments, the method further comprises the preliminary step of maneuvering the tunneling system in the limb along a chosen path to thereby create the subcutaneous tunnel. In some embodiments, passing the blood vessel in the tunneling system lumen is performed after anastomosing a first end of the blood vessel. In some embodiments, cutting means (not shown) are applied to cut down the implantable sleeve to a desired covering length and/or to cut down the blood vessel, after implantable sleeve is in apposition. In some embodiments of the invention, a second end of the blood vessel is anastomosed after withdrawing the tunneling system from the subcutaneous tunnel.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An apparatus, comprising:
an implantable sleeve;
a sleeve expander capable of covering with said implantable sleeve an exterior of a bodily vessel, along a chosen length thereof, said sleeve expander configured to maintain at least a portion of said implantable sleeve in an expanded size greater than a cross sectional dimension of said implantable sleeve when in apposition to said exterior of said bodily vessel, wherein said implantable sleeve is provided at least partially on said sleeve expander; and
a cutting mechanism, operatively connected to, and provided slidably movable in tracks extending along a length of, said sleeve expander, and configured to cut down said implantable sleeve to a covering length corresponding to said chosen length, when in said apposition to said exterior of said bodily vessel.

2. An apparatus according to claim 1, wherein said sleeve expander comprises an internal mandrel enclosing a channel sized to fit over periphery of said bodily vessel, and an external surface having a circumference sized to hold said portion in said expanded size.

3. An apparatus according to claim 2, wherein said channel is 4 mm or more in diameter.

4. An apparatus according to claim 2, wherein said channel is shorter than said chosen length.

5. An apparatus according to claim 1, wherein said sleeve expander comprises at least one leg having a free end detachably connectable to an outer surface of said implantable sleeve, said leg being transferable from a first outward position, in which said portion is in said expanded size, to an inward position, in which said portion is in said cross sectional dimension or is smaller than said cross sectional dimension.

6. An apparatus according to claim 1, wherein said cutting mechanism comprises a blade and a lever adapted for selectively positioning said blade in a chosen tracked position.

7. An apparatus according to claim 6, wherein said blade is rotatable about a longitudinal axis of said implantable sleeve.

8. An apparatus according to claim 1, further comprising a switch for selectively altering said cutting mechanism from a non-cutting mode to a cutting mode.

9. An apparatus according to claim 1, wherein said cutting mechanism is designed and arranged to cut through a wall of said bodily vessel when covered with said implantable sleeve for creating a cut end of said bodily vessel with said implantable sleeve in apposition thereto and flush at said cut end.

10. An apparatus according to claim 1, further comprising a bonding agent introducer having an orifice configured to allow flowing of a bonding agent from a reservoir, connectable to said introducer, to an outer periphery of said implantable sleeve, such that said implantable sleeve, when brought in apposition with said bodily vessel, is bondable to said bodily vessel by said bonding agent.

11. An apparatus according to claim 1, further comprising a stitchery apparatus configured to suture a covering section of said implantable sleeve to a corresponding covered section of said bodily vessel.

12. An apparatus according to claim 1, further comprising a pressing apparatus configured to press a covering section of said implantable sleeve and/or a plastically formable fixator provided thereon, such that said covering section is firmly attached to a corresponding covered section of said bodily vessel.

13. An apparatus according to claim 1, wherein said implantable sleeve comprises a meshed portion.

14. An apparatus according to claim 13, wherein said meshed portion is braided.

15. An apparatus according to claim 13, wherein said meshed portion is knitted.

16. An apparatus according to claim 1, wherein said implantable sleeve is shrinkable to fit in diameter to said bodily vessel when having maximal and minimal outer diameters in between 3 mm to 9 mm, respectively.

17. An apparatus according to claim 1, wherein said portion is extendable from said axially compressed form to an axially extended form.

18. An apparatus according to claim 1, wherein said chosen length is 1 cm to 20 cm.

19. An apparatus according to claim 1, wherein said chosen length is 20 cm to 90 cm.

20. An apparatus according to claim 1, further comprising metering means arrangeable to facilitate measuring of a covering length of said implantable sleeve upon said bodily vessel.

21. An apparatus according to claim 1, wherein said bodily vessel is a native vein or artery.

22. An apparatus according to claim 1, wherein said bodily vessel is a graft.

* * * * *